United States Patent
Melzer et al.

(10) Patent No.: US 6,847,837 B1
(45) Date of Patent: *Jan. 25, 2005

(54) MR IMAGING METHOD AND MEDICAL DEVICE FOR USE IN METHOD

(75) Inventors: Andreas Melzer, Duisburg (DE); Martin Busch, Witten (DE)

(73) Assignee: Simag GmbH, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/529,483

(22) PCT Filed: Oct. 13, 1998

(86) PCT No.: PCT/DE98/03046
§ 371 (c)(1),
(2), (4) Date: Jun. 2, 2000

(87) PCT Pub. No.: WO99/19739
PCT Pub. Date: Apr. 22, 1999

(30) Foreign Application Priority Data

Oct. 13, 1997 (DE) .......................................... 197 46 735

(51) Int. Cl.⁷ .............................................. A61B 5/55
(52) U.S. Cl. ...................... 600/421; 600/422; 600/423; 324/307; 324/309; 324/318; 324/322
(58) Field of Search ................................ 600/410, 420, 600/421, 422, 423, 424, 431, 435; 324/307, 309, 318, 322

(56) References Cited

U.S. PATENT DOCUMENTS

| | | |
|---|---|---|
| 3,731,184 A | 5/1973 | Goldberg et al. .......... 324/34 R |
| 4,815,473 A | 3/1989 | Watson et al. ............... 128/721 |
| 4,960,106 A | 10/1990 | Kubokawa et al. ............ 128/6 |
| 5,057,095 A * | 10/1991 | Fabian ........................ 604/362 |
| 5,160,890 A | 11/1992 | Roschmann ................. 324/314 |
| 5,170,789 A | 12/1992 | Narayan et al. ......... 128/653.5 |
| 5,413,104 A | 5/1995 | Buijs et al. .............. 128/653.5 |
| 5,445,151 A | 8/1995 | Darrow et al. ........... 128/653.3 |
| 5,447,156 A | 9/1995 | Dumoulin et al. ....... 128/653.2 |
| 5,644,234 A | 7/1997 | Rasche et al. ............... 324/318 |
| 5,727,552 A * | 3/1998 | Ryan ........................... 600/407 |
| 5,744,958 A | 4/1998 | Werne ......................... 324/318 |
| 5,964,705 A | 10/1999 | Truwit et al. ............... 600/423 |
| 6,280,385 B1 * | 8/2001 | Melzer et al. .............. 600/423 |

FOREIGN PATENT DOCUMENTS

| | | |
|---|---|---|
| DE | 40 08 202 A1 | 9/1991 |
| DE | 42 38 831 A1 | 5/1994 |
| DE | 195 10 194 A1 | 10/1995 |
| DE | 195 07 617 A1 | 9/1996 |
| EP | 0 385 367 A1 | 9/1990 |
| EP | 0 597 546 A1 | 5/1994 |
| EP | 0 602 970 A2 | 6/1994 |
| EP | 0 673 621 A1 | 9/1995 |
| EP | 0 768 539 A2 | 4/1997 |
| EP | 0 775 500 A1 | 5/1997 |
| WO | WO 96/38083 | 12/1996 |

OTHER PUBLICATIONS

E. Fukushima et al, "Experimental Pulse NMR a Nuts and Bolts Approach", NMR Hardware, V.C.6. Crossed Diodes, pp. 388–392.

M. Burl et al., "Tuned Fiducial Markers to Identify Body Locations with Minimal Perturbation of Tissue Magnetization", Tuned Fiducial Markers, 1996, XP 000624684, pp. 491–493.

* cited by examiner

*Primary Examiner*—Eleni Mantis Mercader
(74) *Attorney, Agent, or Firm*—Christie, Parker & Hale, LLP

(57) ABSTRACT

The invention relates to an MR imaging method for representing and determining the position of a medical device inserted in an examination object, and to a medical device used in the method. In accordance with the invention, the device (11) comprises at least one passive oscillating circuit with an inductor (2a, 2b) and a capacitor (3a, 3b). The resonance frequency of this circuit substantially corresponds to the resonance frequency of the injected high-frequency radiation from the MR system. In this way, in a locally limited area situated inside or around the device, a modified signal answer is generated which is represented with spatial resolution.

42 Claims, 10 Drawing Sheets

MR IMAGING METHOD AND MEDICAL DEVICE FOR USE IN METHOD

FIELD OF THE INVENTION

The invention relates to an MR (magnetic resonance) imaging method for representing and determining the position of a medical device inserted in an examination object according to the generic part of claim 1 and a medical device for use in the method.

BACKGROUND OF THE INVENTION

MR imaging methods have been known for some time. They are based on the resonance alternating effect between a high-frequency (HF) electromagnetic alternating field and specific atomic nuclei of an object to be examined, in particular a human or an animal body that is arranged in a strong external magnetic field. The atomic nuclei precess in the magnetic field ($B_0$) by the so-called Lamor frequency that is proportional to the strength of the magnetic field. When applying an electromagnetic alternating field whose magnetic alternating component ($B_1$) is perpendicular to the direction of the strong magnetic field ($B_0$), the spins of the atomic nuclei flip and associated relaxation times may thus be measured.

In the description of a scientific model, the magnetization of the individual spins is described by total magnetization. This total magnetization in its equilibrium condition is parallel to the external magnetic field and is called equilibrium magnetization. By means of an HF-impulse applied with the Lamor frequency (resonance frequency), the magnetization may be deflected by an angle $\alpha$ with regard to the direction of the magnetic field. The angle $\alpha$ is proportional to the time period of the HF-impulse applied and the strength of the magnetic field ($B_1$) of the HF-impulse. Subsequent to an excitation by the angle $\alpha$, the total magnetization precesses around the direction of the magnetic field. The precessing magnetization may be recorded by a coil that is oriented perpendicularly to the direction of the magnetic field, in form of a voltage signal. The strength of the voltage signal is proportional to $\sin(\alpha)$, proportional to the density of the spins in the signal emitting volume and inversely proportional to the temperature.

The maximal signal response of a given volume is thus attained after 90° excitation. The recorded signal amplitude decreases exponentially with the relaxation time $T_2^*$, since the individual spins fall out of phase due to the fluctuating magnetic fields. Simultaneously, the total magnetization increases exponentially again in the direction of the magnetic field towards the equilibrium magnetization with relaxation time $T_1$. By means of magnetic gradient fields switched at the correct point in time, it is possible to image differentiated combinations from the spin density and the two relaxation times in a gray scale encoded image with spatial resolution.

It is further known to locally induce an amplification of the excitation of the nuclear spins by means of a resonance circuit. For this, so called "fiducial markers" are known that have compartments filled with special signal-intensive liquids surrounded by a resonance circuit. (Burl et al.: "Tuned Fiducial Markers To Identify Body Locations with Minimal Perturbation of Tissue Magnetization", in: Journal of Magnetic Resonance in Medicine 1996, p. 461–493.) The resonance circuit has the resonance frequency of the MR system.

If such a fiducial marker is brought into the imaging volume of a nuclear magnetic resonance tomograph, the resonance circuit is excited when electromagnetic radiation is applied at resonance frequency. This results in amplification of the magnetic alternating field within the inductance of the resonance circuit. The increased magnetic component of the magnetic field increases the deflection angle $\alpha$ of the protons within the inductance. With a small angle of excitation ($\alpha<90°$) of the protons by the nuclear spin system, the protons experience an increased excitation angle within the inductance. In the ideal case, protons are excited with a small angle of 1 to 10° in the imaging volume, whereas the protons within the inductance are excited with 90°. Even with identical relaxation times and with an identical spin density, the signal from the compartment surrounding the resonance circuit is clearly more intensive than the signal of the other parts of the image. Since this signal amplification is localized, it may be used to determine positions.

According to the law of reciprocity, it is also true that the MR response signals of the protons within the compartment surrounding the resonance circuit (fiducial markers) are amplified. Due to the inductance, the magnetic field lines originating from the spins within the coil are bundled such that more signal is emitted from the volume within the inductance and applied to a associated receptor coil. This amplification of emitted and then received signals is considered independent of an increased excitation. Both effects result in a changed signal response of the fiducial marker.

Disadvantageously, fiducial markers make use of separate signal emitting volumina, which for visibility in the MR image must be at least a few cubic millimeters in size and must be placed specifically in the examination object or must be integrated into the systems that are placed in the examination object. Often this is not possible.

With the introduction of open magnets and new techniques with closed MR systems, it has become possible to carry out interventional and minimally invasive techniques such as punction, catheterization and surgical processes under MR tomographic control. However, ferromagnetic or paramagnetic metals or impurities in other materials result in artifacts in the images.

Problems result from the tools used for interventional and minimally invasive techniques since they usually consist of ferromagnetic or paramagnetic material and/or that they are so small that they are about the size of one pixel (ca. 1 mm) in MR images. In particular, catheters and implants made of metal or plastics are frequently not visible in the MR image and can best be located by means of artifacts. When materials that are not visible in the MR image are used, they can be seen only as "shadows." These disadvantages result in the fact that MR monitoring of interventional and minimally invasive techniques is frequently unsatisfactory and that an x-ray method with all its known disadvantages is used instead for imaging.

From DE 195 10 194 A1 an active-invasive magnet resonance system for the production of selective MR angiograms is known, whereby an invasive apparatus is provided with an HF coil by which the nuclear spin magnetization of the blood flowing in the vessel is changed locally. By means of special MR image impulse sequences, only the blood that has a changed nuclear spin magnetization is selectively detected and imaged.

U.S. Pat. No. 5,445,151 describes a method for flow measurements in flowing fluids, in particular in blood, whereby the invasive apparatus is provided with at least two HF coils, whereby a local change in nuclear spin magnetization produced by one HF coil is sensed at the other HF coil and the delay interval is used for the computation of flow velocity.

The two publications cited above do not refer to the imaging of medical apparatuses introduced into a body. Furthermore, they have the disadvantage that they are active systems whereby the apparatuses introduced are permanently connected via cable connections to extracorporeal components.

Patent publication DE 195 07 617 A1 describes an MR method whereby a surgical instrument, such as a catheter, is introduced into an examination object whereby the catheter is provided with a micro-coil at its point. The position of the micro-coil is determined by specific sequential techniques.

EP-A-0 768 539 discloses an MR method for determining the position of an object which has been introduced into the body of a patient. A coil arrangement without connection to extracorporeal components is attached on the object to be introduced into the body, for instance, a catheter or a surgical instrument, and a signal change which occurs due to the coil is used to determine the location of the object.

SUMMARY OF THE INVENTION

The object of the present invention is to provide an MR imaging method for representing and determining the position of an unfoldable medical device, defined herein as a medical device that at least in part is capable of being unfolded when introduced into an examination object and to provide a medical device suitable for use in the method which allows for clear, signal-intensive imaging of the device in the MR image.

To accomplish this object, the invention is characterized by an MR imaging method for imaging and determining the position of a medical device, such as an unfoldable vena cava filter or balloon catheter, inserted into an object being examined. The object is arranged in an external magnetic field, high-frequency radiation of a specific resonance frequency is applied, transitions between spin energy levels of the atomic nuclei of the object are excited, and MR signals are produced and detected as signal responses, evaluated, and imaged in spatial resolution. In a locally defined area inside and/or outside the device, a changed signal response of the object is produced whereby the device has or forms at least one passive resonance circuit with an inductor and a capacitor so that their resonance frequency is essentially equal to the resonance frequency of the applied high-frequency radiation. An unfoldable part of the device forms the inductor or is integrated therein. This unfoldable part is unfolded after insertion of the device into the object, and the area is imaged with the changed signal response in spatial resolution.

The invention is also characterized by a medical device, such as an unfoldable vena cava filter or balloon catheter, having at least one passive resonance circuit with an inductor and a capacitor, whose resonance frequency is essentially equal to the resonance frequency of the applied high frequency radiation of an MR imaging system. An unfoldable part of the device forms the inductor, or the inductor is integrated into such a part, so that it unfolds along with the device when the device is unfolded. Advantageous and preferred embodiments of the invention are reported in the dependent claims.

To accomplish this object, provision is made in the invention to integrate a resonance circuit into the medical device to be introduced into the examination object such that an unfoldable part of the device forms the inductor or the inductor is integrated into such a part, such that it unfolds along with the device when this is unfolded. In a locally defined area inside and/or outside the device, a changed response signal of the examination object is induced that is imaged by spatial resolution. The resonance frequency of the resonance circuit is essentially equal to the resonance frequency of the applied high-frequency radiation of the MR imaging system. Since that area is immediately adjacent to the device from inside or outside, the position of the device is clearly recognizable in the correspondingly enhanced area in the MR image. Because a changed signal response of the examined object is induced by itself, only those artifacts appear that are produced by the material of the device itself.

Due to the clear imaging of the device in the MR image, a precise position determination is possible. Furthermore, based on the changed signal conditions, improved flow measurement is now possible in the case of a fluid flowing through the device or past the device. Use is made of the fact that different excitation is present inside and outside the device.

The object of the present invention is accomplished, as it is based on the surprising discovery that suitable resonance circuits can be formed on or integrated into the device and also upon the unfolding of the device. This makes available a compact device which ensures improved imaging in the MR image even with the presence of unfoldable parts of the device. Moreover, a synergistic effect develops. The invention preferably provides that the inductor and capacitor providing the resonance circuit are formed by the material of the device, thereby resulting in an additional synergistic effect. It is also within the framework of this invention to provide inductors and capacitors as separate components on the device.

According to the invention, the signal response of the spins within the inductor is changed. Two processes contribute to this. On the one hand, the resonance circuit tuned to the resonance frequency is excited by the application of high-frequency radiation and the nuclear spins detected by the field of the resonance circuit experience amplified excitation through local amplification of the alternating magnetic field in or near the inductor. In other words, protons detected by the field lines of the induced magnetic field are deflected at a larger angle than the protons on the outside of this induced magnetic field. An increased flip of the nuclear spins results. Accordingly, the signal response sensed by a receptor coil and evaluated for imaging can be amplified. It is furthermore possible that only the spins within the inductor experience saturation and that the signal is diminished with regard to the environment. In both cases, a change in signal response is apparent.

On the other hand—independent of amplified excitation—the MR response signals of the protons within the inductor are amplified. The inductor thus bundles the magnetic field lines originating from the spins within the inductor, which results in an amplified signal emission and an application to an associated receptor coil that receives the amplified signals and transmits them for MR imaging. This effect is described in the publication by J. Tanttu: "Floating Surface Coils", in: XIV ICMBE AND VII ICMP, Espoo, Finland 1985.

According to the present invention, both of these effects may be used in the process of changing the signal response. However, the second effect, i.e., an amplification of the MR response signal, may also be used alone.

Accordingly, a first embodiment of the present invention is characterized in that the application of high-frequency radiation excites the resonance circuit, thus resulting in an amplified excitation of the nuclear spins in the locally defined area.

The locally defined area in which an amplified excitation of the nuclear spins take place may, on the one hand, be located in a compartment formed within the device and surrounded by the inductance. Thus, a volume of the examination object arranged in the interior of the inductor or coil is more strongly imaged. For this, provision is made in particular that the device is elongated and that the axis of the inductance coil runs substantially parallel to the longitudinal axis of the device, whereby the inductor is formed in or on the surface of the device.

On the other hand, this area can be located outside the device and adjacent thereto, whereby at least one resonance circuit is arranged on the surface of the device such that with the application of high-frequency radiation the magnetic flow in the adjacent area observed is amplified. Preferably, the coil axis runs substantially parallel to the longitudinal axis of the device. This variant uses the surrounding medium for signal amplification. However, combinations of the two aforementioned variants are also possible.

A second embodiment of the invention provides that with the application of the high-frequency radiation, the resonance circuit becomes detuned or the capacitor is short circuited such that no enhanced excitation of the nuclear spins takes place in the locally defined area. However, during measurements of the signal response of the locally defined area, the detuning of the resonance circuit or the short circuiting of the capacitance is canceled again, thus causing the resonance circuit to provide an amplification of the radiated MR response signals of the protons. It was in particular found that this variant makes possible the imaging of the area in and around the device with high quality, i.e., that it provides local imaging beyond the pure position determination. In addition to the position of the device, the MR image provides improved information regarding the structure, etc. of the inside and/or the environment of the device.

An amplification of the excitation of the nuclear spins is, for example, suppressed, in that the condenser (capacitor) of the resonance circuit is short circuited during excitation by means of crossed diodes. The amplification of the emitted signals is thus not influenced, since the small induced voltage from the spins within the inductor is below the conducting-state voltage during emission.

General reference is made to the fact that the change of the signal response according to the invention will usually be an amplification of the signal response. However, this depends on numerous factors, in particular on the excitation sequences used. For instance, with quick consecutive sequences it is possible that a saturation of the excitation of the spins within the inductor is present, thus no signal is produced there. There is, however, no saturation present in the area outside of the inductor, where a smaller excitation of the nuclear spins takes place, thus a signal is produced here. Correspondingly, in this example, a decrease in the signal response occurs in the area detected by the field of the inductance.

A preferred embodiment of the invention provides that the resonance circuit is adjusted to the resonance frequency after insertion of the device into the examination object by unfolding the device. For example, in the case of a balloon catheter, the inductor unfolds with the inflating of the balloon catheter, whereupon the resonance circuit is adjusted.

Advantageously, inductance and/or capacitance are adjustable for resonant tuning of the resonance circuit.

This makes sense if after introduction of the device into the examination object and a possible expansion of the device or parts of the device, the product of inductance and capacitance, and thus the resonance frequency of the resonance circuit, change.

In an advantageous embodiment of the present invention, at least two resonance circuits are formed or arranged on the device, whereby the coils of the respective inductors are differently aligned, in particular arranged perpendicular relative to each other or arranged behind each other. Coils aligned perpendicular relative to each other ensure that in every arrangement of the device in the outer magnetic field, one component of the inductance runs perpendicular to the field direction of the outer magnetic field, such that a changed signal response is guaranteed. In addition, using suitable sequence techniques, coils arranged behind each other are particularly suited to carry out a flow measurement (i.e., determination of velocity) of a fluid flowing through or past the device.

Provision is made in a further development of the invention that the inductor of the device is optionally also used as a receptor coil for the acquisition of MR response signals, whereby the inductor is connected by means of a cable link with extracorporeal functional components. This enables also using the inductor known from the previously developed methods actively for imaging.

An MR imaging system according to the invention for performance of the imaging process includes a conventional imaging system and a medical device where the inductor is formed or arranged on the surface of the device.

DESCRIPTION OF THE DRAWINGS

Several exemplary embodiments of the invention are explained in the following in detail with reference to the drawing. They depict.

DETAILED DESCRIPTION OF THE INVENTION

Figure 1B:
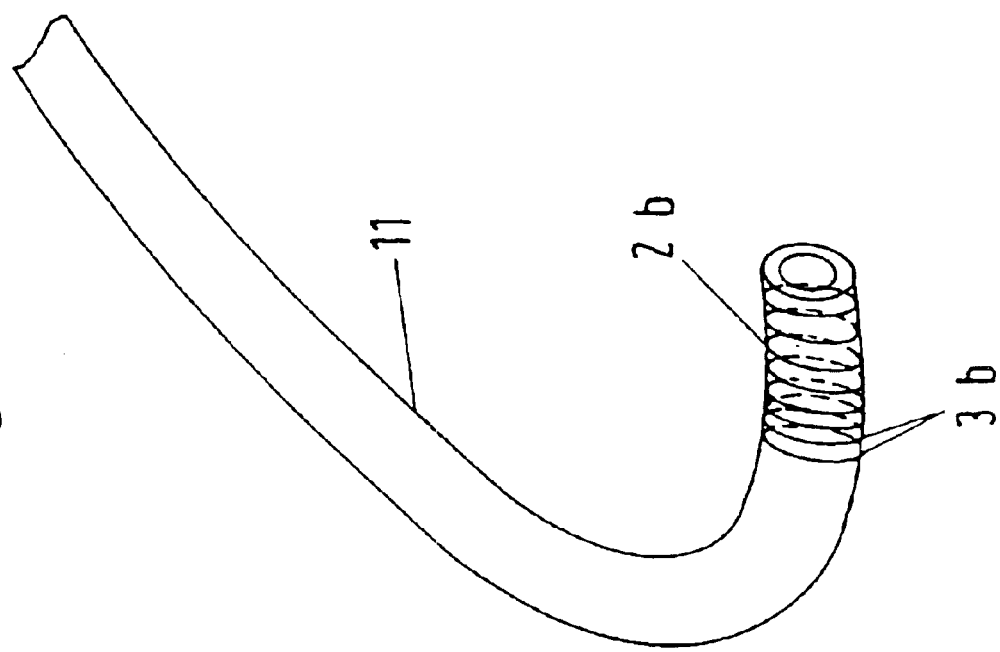
FIGS. 1a and 1b—schematically, two exemplary embodiments of a catheter or guide wire designed according to the invention.
Figure 1A:
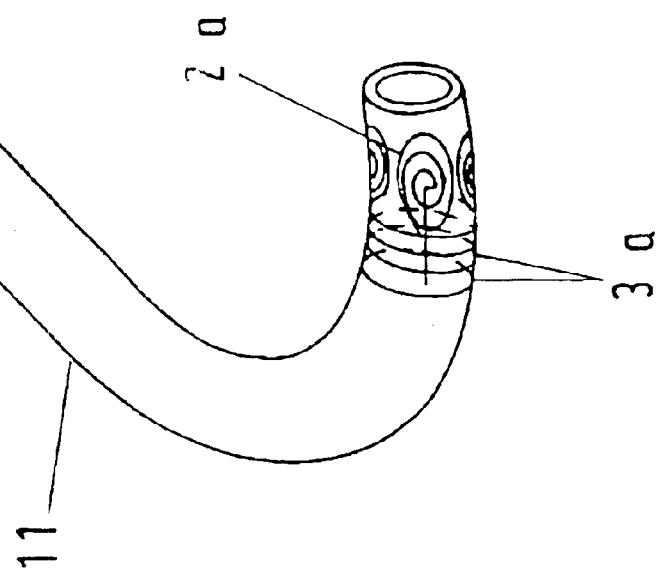

FIGS. 1a and 1b depict a guide wire or catheter 11, on the point of which a resonance circuit consisting of an inductor 2a, 2b and a condenser 3a, 3b is in each case formed. In FIG. 1a, the inductor is formed by a spiral-shaped conductor 2a (solenoid coil) such that the induced magnetic field is aligned substantially perpendicularly relative to the catheter 11 in the surrounding tissue and causes amplified excitation of the nuclear spin there. In FIG. 1b, the inductor is formed by a helix-shaped coil 2b such that the induced magnetic field runs substantially parallel to the longitudinal axis of the catheter 11 and caused amplified excitation of the nuclear spin in the inside of the catheter 11. The condenser 3a, 3b is in each case implemented by parallel, annular conductor elements. Alternatively, the condenser may also be implemented by a separate structural element which is integrated into the catheter 11.

The inductor 2a, 2b and the capacitor 3a, 3b are preferably formed on a foil, for instance, by means of a photo-lithographic process. The foil is applied to a flexible hose (not depicted separately). After sealing of the hose and the foil, the hose is applied to the guide wire or catheter 11 such that the arrangement depicted results.

In other embodiments (not depicted) a plurality of resonance circuits according to FIG. 1a, 1b are arranged along the guide wire or the catheter 11.

Figure 2A:
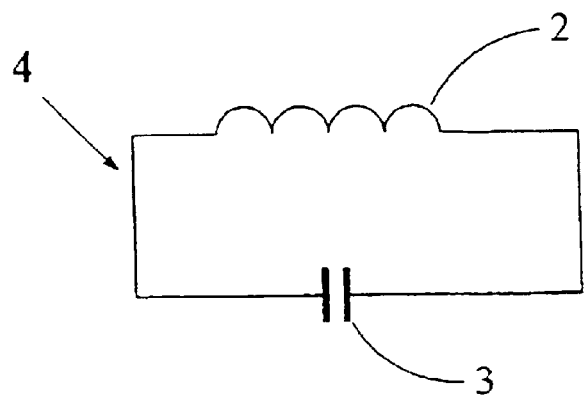
FIGS. 2a–2g—various electrical diagrams of a resonance circuit according to the invention.
Figure 2B:
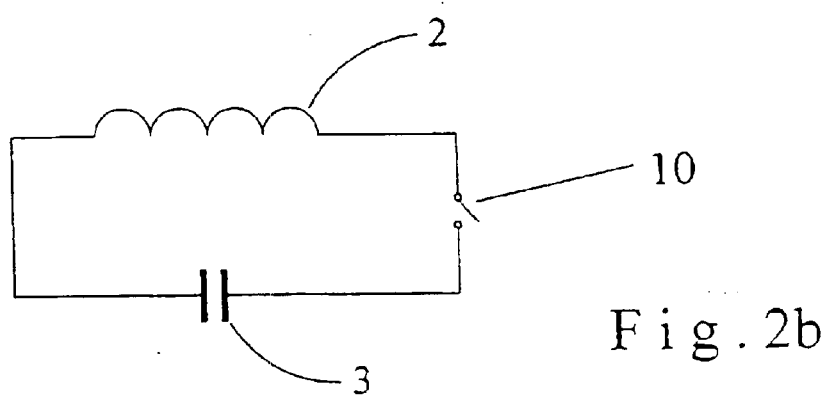

FIG. 2a discloses the electrical diagram of the resonance circuit 4 provided in the catheter 11, consisting of inductor 2 and capacitor 3. According to FIG. 2b, an optional additional switch 10 is provided, which can be activated or deactivated electrically or magnetically or, for instance, mechanically by means of an activation wire of the catheter 11.

Figure 2C:
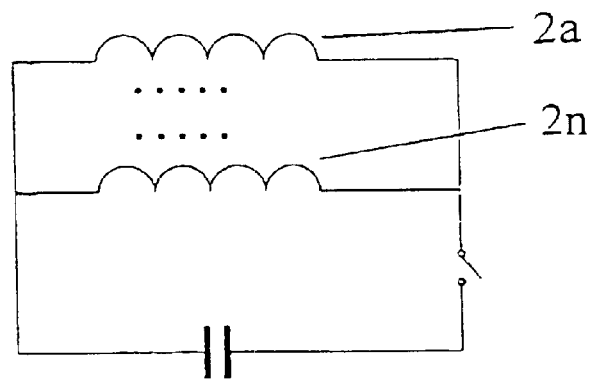
Figure 2D:
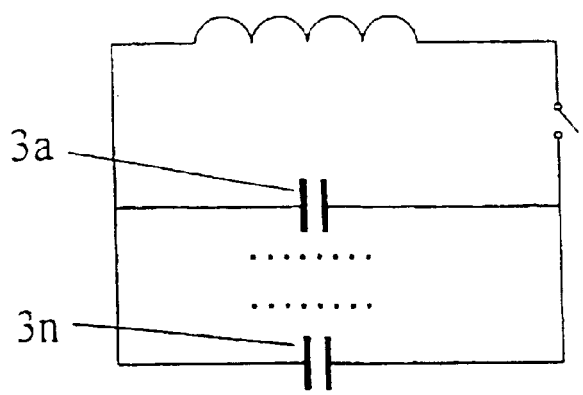

The resonance circuit 4 can be designed in a great variety of embodiments. According to FIG. 2c, it may have several parallel switched inductors 2a to 2n, and according to FIG. 2d it may have several parallel switched capacitors 3a to 3n. Furthermore, several inductors and/or capacitors may be serially switched. Several resonance circuits may also be provided on one device which may each have a switch and may have serially and/or parallel switched inductors and/or capacitors.

The resonance circuit 4 has a resonance frequency that corresponds to the high frequency radiation applied to the MR imaging system in which the human body into which the catheter is inserted, is placed.

In the catheter 11 according to the invention, the resonance circuit 4 is excited by the applied high-frequency pulses of the MR system, since its resonance frequency corresponds to the frequency of the applied HF-pulse. This results in amplification of the magnetic field in the inductor of the resonance circuit, or near the inductor, which again may result in an amplified excitation of the protons in the corresponding area. In an excitation of the nuclei outside the area detected by the magnetic field of the inductance by an angle that is smaller than 90°, nuclei within the area detected by the magnetic field of the inductor may experience an excitation of 90° and thus respond at a maximum amplitude. The protons or nuclei arranged in the area of the inductor thus experience a stronger excitation than the protons arranged outside the inductor.

The increase in the deflection angle within the inductor or in the area detected by the magnetic field of the inductance may be up to a factor of 45 in comparison with the protons outside the magnetic field of the inductance. It is therefore possible to deflect the protons inside the inductance by an angle of 90° (max. signal response), whereas the protons outside the inductance or outside the magnetic field produced by the resonance circuit, experience no more than a small angle excitation of 2° to 10°. This results in the fact that in the case of FIG. 1b the inside area of the catheter 11 and in the case of FIG. 1a the area adjacent the catheter 11 is imaged substantially brighter in an MR image than the rest of the area. Therefore, the location of the catheter 11 in the human body can be precisely determined.

An estimate of the required capacitances and inductances follows for the further disclosure of details of the invention.

In the exemplary embodiment, a plate condenser is used and the inductance coil is assumed to be a helix with a fixed number of turns. The resonance frequency of a nuclear spin system is usually in the range between 2 MHz to 90 MHz. The resonance frequency of the nuclear spin system is equal to the product of the magnetic field strength and the gyromagnetic relationship g. At a medium field strength of 1 tesla, a resonance frequency of about 42 MHz results. The resonance frequency of the resonance circuit is determined by Thomson's resonance equation. It is inversely proportional to the root of the product of the inductance and the capacitance.

The product of conductance and capacitance thus is equal $1.4 \times 10^{-19}$ $S^2$. Depending on the number of turns and the catheter 11 of FIG. 1b having an assumed diameter of 8 mm and an inductance coil 2b of a 40 mm length, an inductance of approximately $4 \times 10^{-6}$ Vs/A results. The resultant surface of a plate condenser with a relative dielectric constant of 2 and a distance of 0.1 mm between the individual plates is approximately 0.2 $mm^2$. Such a small surface of a plate condenser is easily realized in a catheter. With stronger magnetic fields or frequencies, the resultant surface of a plate condenser can be further reduced to 0.014 $mm^2$.

Figure 2E:
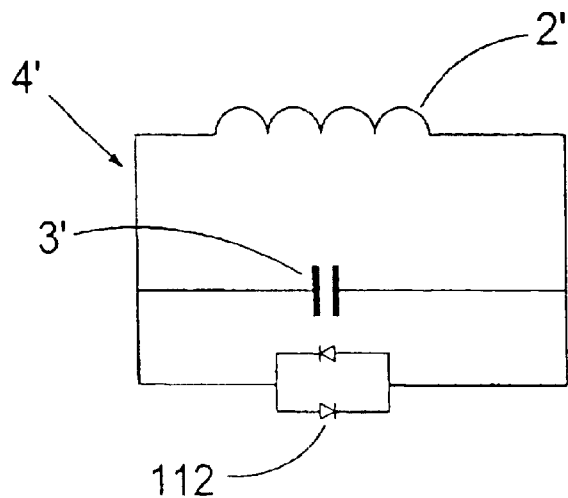
Figure 2F:
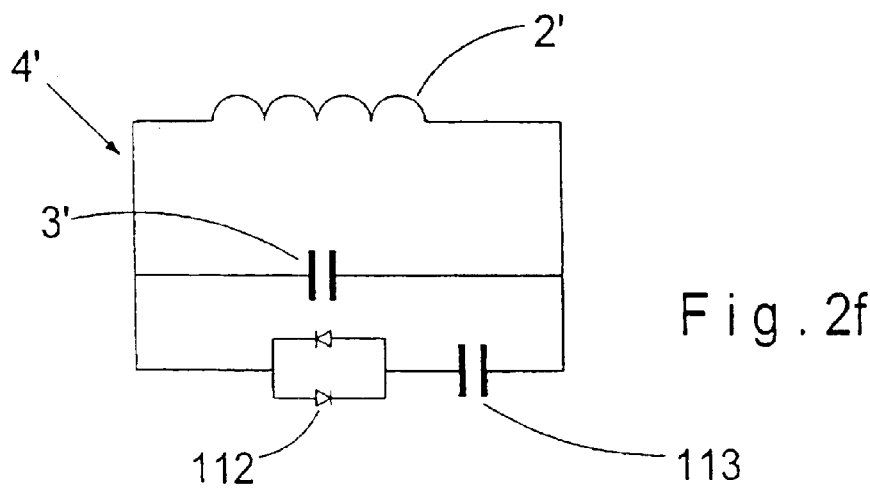
Figure 2G:
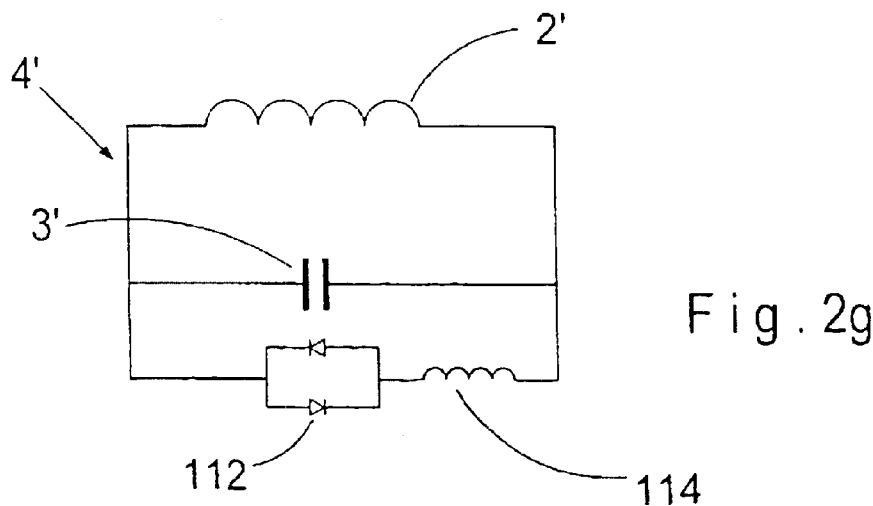

Two additional variants of the invention are disclosed in the diagrams of FIGS. 2e through 2g. In FIG. 2e the condenser 3' is short circuited during the excitation phase by means of two crossed diodes 112 that are provided as additional elements in the catheter. The diodes 112 have a conducting-state voltage of approximately 1 Volt, that is, in any case, below the voltage produced by the application of high-frequency radiation which usually is above 1 Volt. The diodes 112 thus are conductive with the application of high-frequency radiation such that the condenser 3' is short circuited in the excitation phase and thus no resonance circuit is formed.

This means, in contrast to the previous exemplary embodiments, that no increased local excitation of the nuclear spins takes place when high-frequency radiation is applied. However, when measuring the signal response of the region sensed by the inductor 2', the short circuit of the capacitance 3' is canceled again. For this purpose, the diodes 112 are formed in such a manner, that the conducting-state voltage is above the voltage produced during the spin signal response.

Thus, the condenser 3' is not short circuited during the emission of MR response signals of the atomic nuclei and a resonance circuit 4' is formed that effects an amplification of the emitted MR response signals of the protons and thus changes the measured signal response.

The diodes 112 may be realized in a large variety of ways in the catheter. In particular, separate components may be used or the diodes may be formed by or in cooperation with the catheter material, for instance, as a structure mounted on the catheter.

With structures that are in principle the same as those disclosed in FIG. 2e, the condenser 3' in FIG. 2f is not short circuited, but rather the resonance circuit 4' is only detuned in the excitation phase by connecting an additional condenser 113, such that an amplified excitation of the nuclear spins takes place to a limited extent only. During the emission of MR response signals, the diodes 112 lock such that the resonance circuit 4' is not detuned now and an amplification of the emitted MR response signals takes place, which results in a changed signal response that is imaged in the MR image.

In FIG. 2g the resonance circuit 4' is not detuned by connecting a condenser but by connecting a coil 114.

It is noted that a short circuiting or a detuning of the resonance circuit can be realized in the excitation phase with any resonance circuits formed or arranged on a medical device, in particular on the devices of FIG. 3a through 9b described in the following.

Figure 3A:
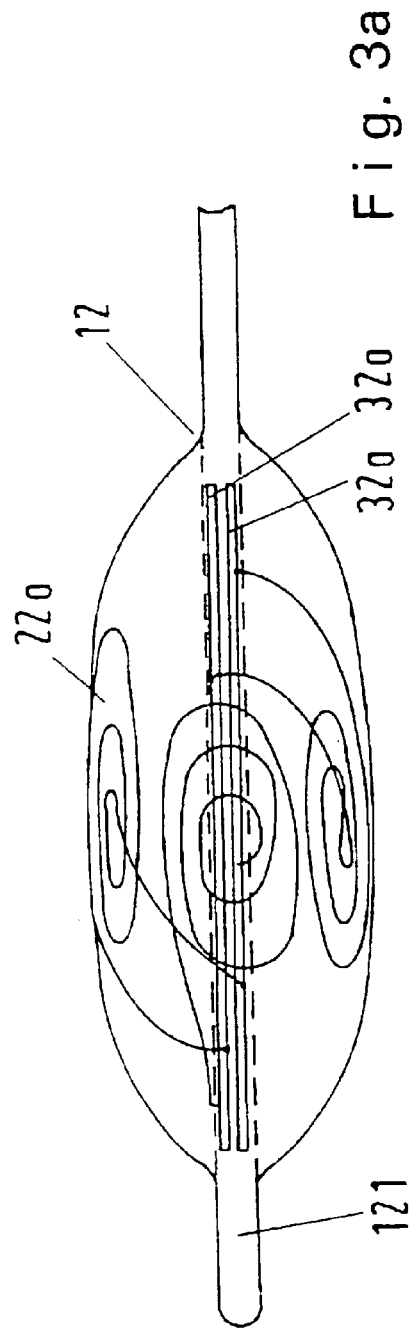
FIGS. 3a and 3b—two exemplary embodiments of a balloon catheter designed according to the invention.
Figure 3B:
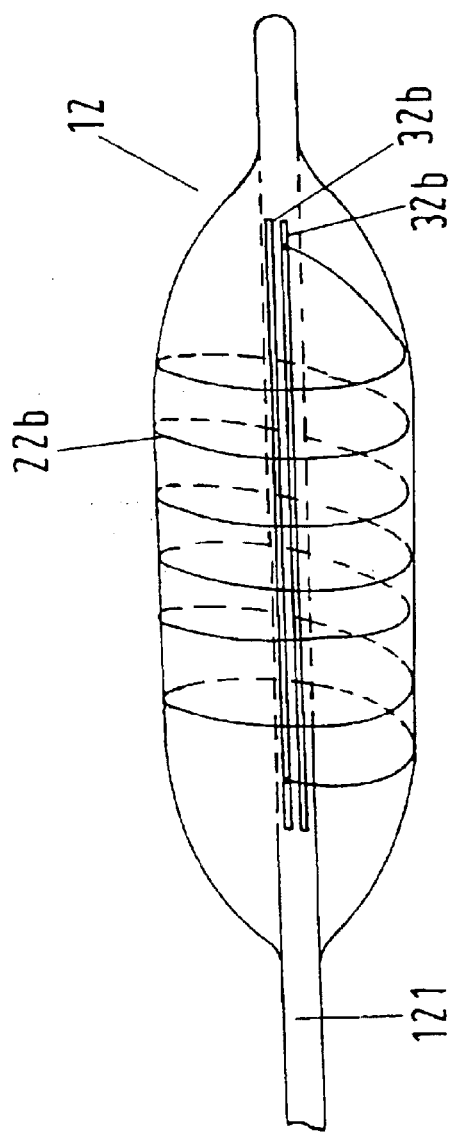

FIG. 3a, 3b depict in each case a balloon catheter 12 with a resonance circuit. In FIG. 3a, a plurality of spiral-shaped inductors 22a, the axes of which run perpendicular relative to the longitudinal axis 121 of the balloon catheter, are mounted on the outer skin of the balloon catheter. In FIG. 3b, a helix-shaped inductor 22b, the axis of which runs parallel to the longitudinal axis 121 of the balloon catheter, is provided. Capacitors 32a, 32b are realized in each case on the axis 121 of the balloon catheter 12 in the form of parallel conductors. The inductors 22a, 22b are, for example, formed on a foil, as described in reference to FIG. 1a, 1b.

Various designs of the resonance circuit are possible for the tuning of the resonance frequency of the resonance circuit to the frequency of the applied HF pulse.

In one variant, provision is made that the quality of the resonance circuit is kept relatively low in order to realize a resonance circuit with the broadest possible bandwidth and thus to cover the largest possible range of resonance frequencies.

A second variant discloses providing an apparatus with the capability to keep the product of inductance and capacitance constant even after a change of the geometry as was observed in the example referring to the inflation of the balloon catheter 12. This may take place either in that the balloon catheter is given a geometry that changes its properties as little as possible during unfolding of the balloon catheter, i.e., in particular, it has a constant inductance and a constant capacitance. An inflation of the balloon catheter at the application location thus substantially causes no change in the resonance frequency of the resonance circuit.

Constancy of the product of inductance and capacitance may be realized, among other things, by a compensation of the changing inductance by a correspondingly changing capacitance. For instance, provision is made that the condenser surfaces are arranged to be movable perpendicular or parallel to each other for compensation of a changing inductance by a correspondingly changing capacitance, such that the capacitance increases or decreases according to the corresponding distance between the condenser surfaces. For instance, in FIG. 3b, longitudinal movability of the two condenser plates 32b at the time of inflation of the balloon catheter can be provided to compensate for the change in inductance at the time of inflation.

A third variant provides that an adjustment of the resonance circuit in the magnetic field of the nuclear spin tomograph is induced by a change or adjustment of the inductance and/or the capacitance of the resonance circuit after their placement. For example, a change of the condenser surface is provided by means of the application instrument located in the body. A decrease in the inductance and thus an adjustment of the resonance circuit to the resonance frequency in the nuclear spin tomograph may take place, for instance, by a laser induced mechanical or electrolytic insulation of coil segments. A change in the capacitance may also take place by a laser induced mechanical or electrolytic insulation of the capacitance.

Figure 4:
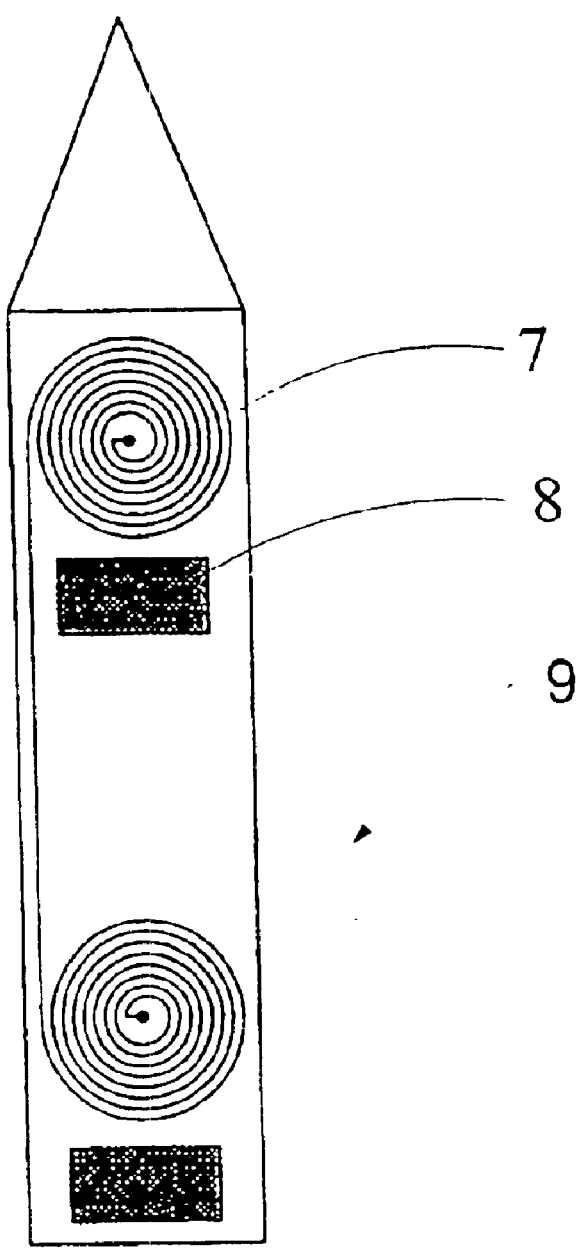
FIG. 4—a medical instrument with resonance circuits mounted on the sides of the instrument.

FIG. 4 depicts an invasive instrument 9, whereby a plurality of resonance circuits, each consisting of an inductor 7 and a condenser 8, are disposed on the lateral surfaces of the instrument 9. The inductor 7 is designed as a spiral-shaped conductor. This results in the fact that the induced magnetic field is aligned perpendicular to the instrument 9 in the surrounding tissue. Thus, amplification of the excitation is undertaken in the external area adjacent the resonance circuit. In the MR image, the interior of the instrument is not enhanced, but rather the surroundings of the instrument, whereby the position of the instrument is, however, equally easy to identify.

Figure 5:
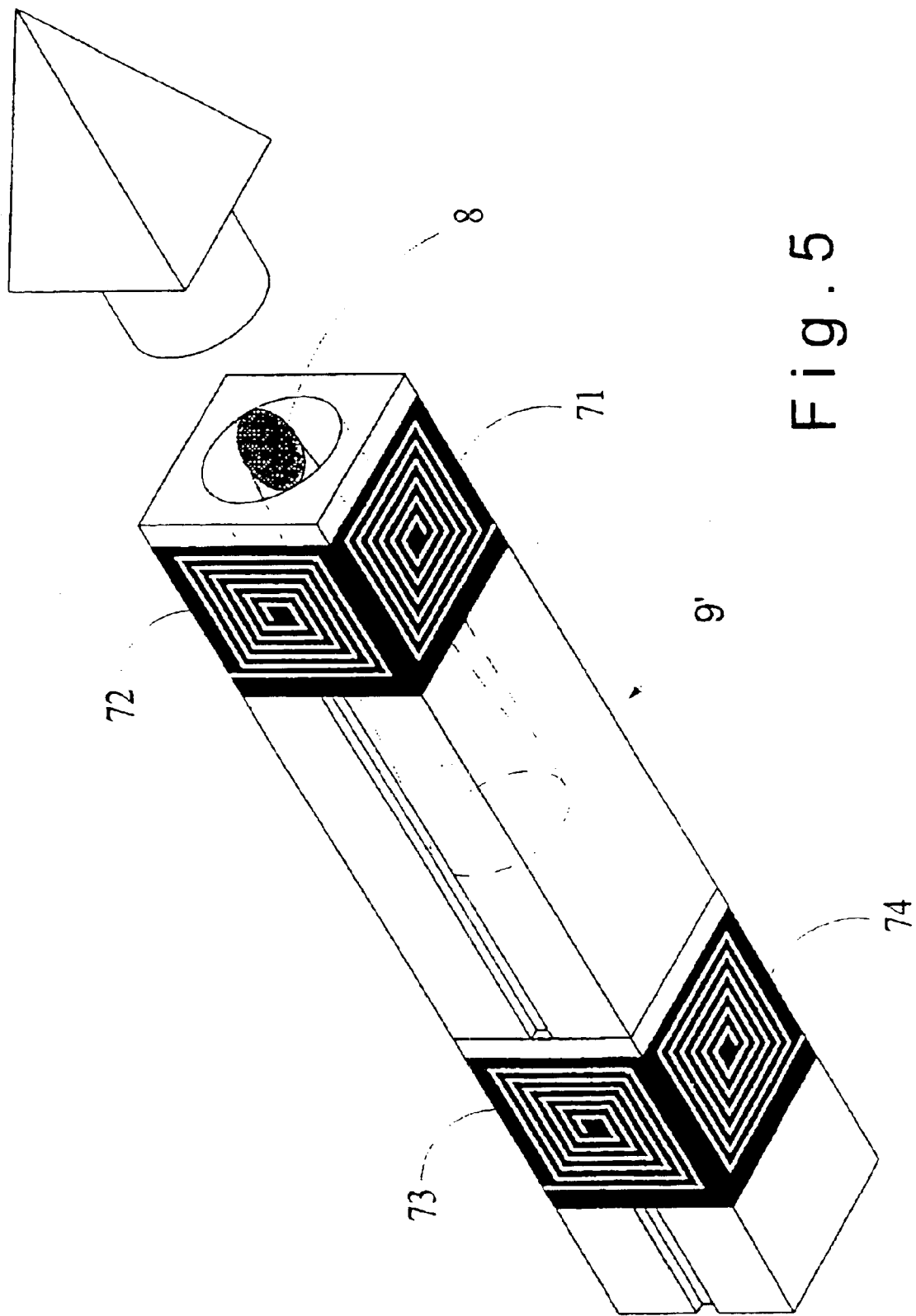
FIG. 5—a perspective depiction of an alternative embodiment of the medical instrument of FIG. 4.

FIG. 5 depicts an alternative embodiment of the instrument of FIG. 4 in a perspective view, whereby it is discernible that on each side of the square-shaped instrument, a spiral-shaped coil arrangement 71, 72, 73, 74 is provided, which forms a resonance circuit along with a schematically depicted condenser 8. The induced magnetic field runs in each case perpendicular to the longitudinal axis of the instrument 9'. The induced magnetic field causes amplified excitation of the nuclear spin in the external area adjacent the instrument penetrated by the magnetic field lines, such that in the MR image, this surrounding area can be enhanced and thus it is possible to determine the position of the instrument.

Figure 6B:
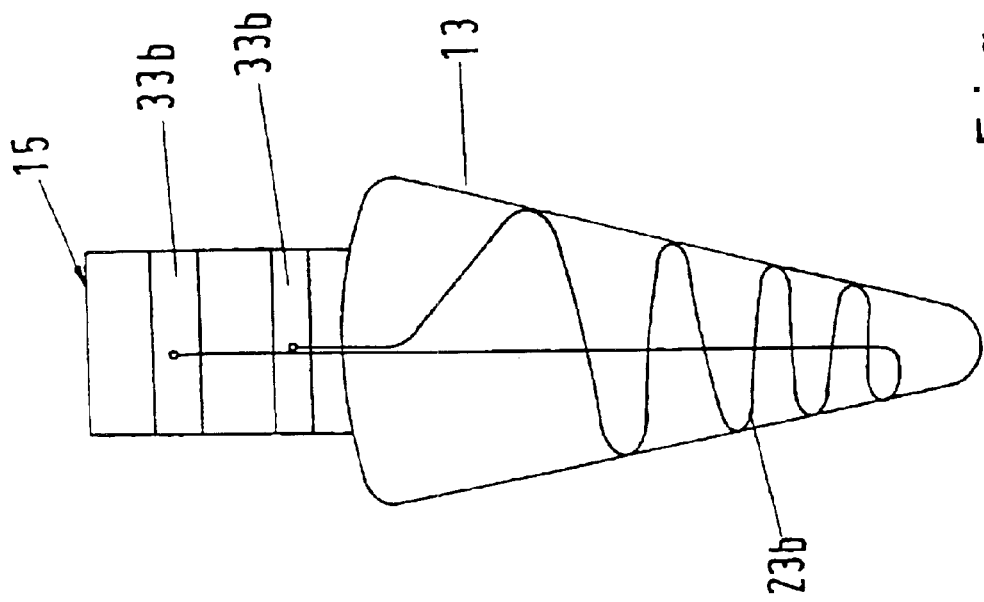
FIGS. 6a and 6b—two exemplary embodiments of a dental implant designed according to the invention.
Figure 6A:
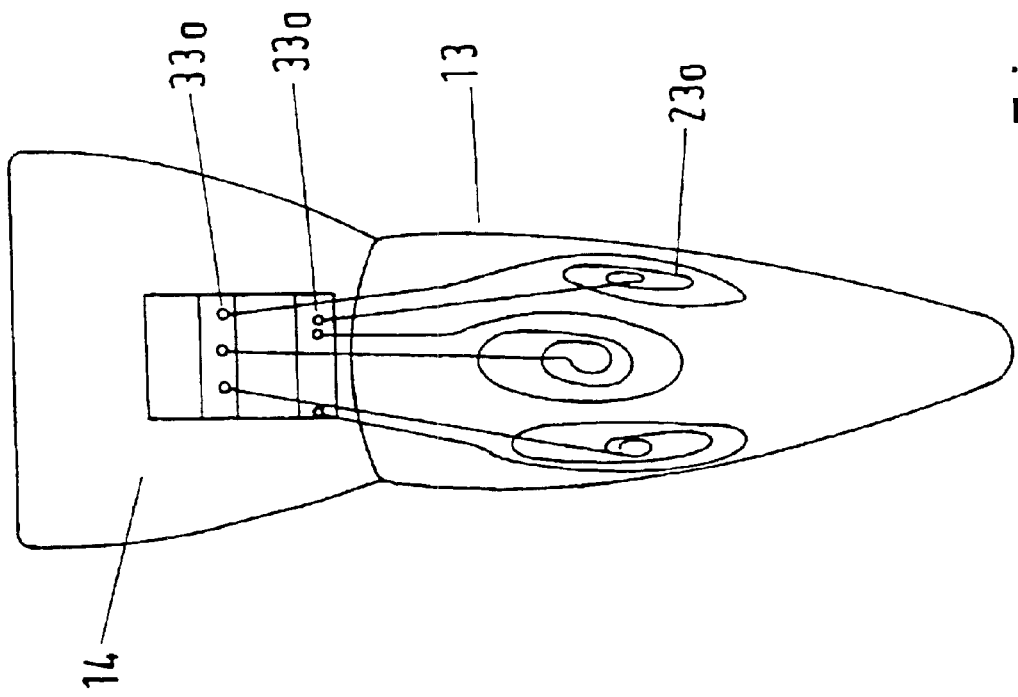

In FIGS. 6a and 6b, a resonance circuit according to the invention is formed on a dental implant 13, whereby the axes of the inductors 23a, 23b again run perpendicular (FIG. 6a) or parallel (FIG. 6b) to the longitudinal axis of the dental implant. The condenser 33a, 33b is formed by parallel annular conductors. FIG. 6a depicts the dental implant with a tooth 14 set on it and FIG. 6b with the contact point 15 still free.

The inductors and capacitors can again be formed on a foil, which is mounted on the dental implant 13 after sealing. Alternatively, the inductor and/or capacitor can be made of wire or cut from a metal sheet. In a preferred variant, the dental implant 13 is formed as a composite material and the inductor and/or capacitor is incorporated into the material of the dental implant. Arranging the inductive or capacitive elements on the surface of the dental implant 13 is thus avoided.

Figure 7A:
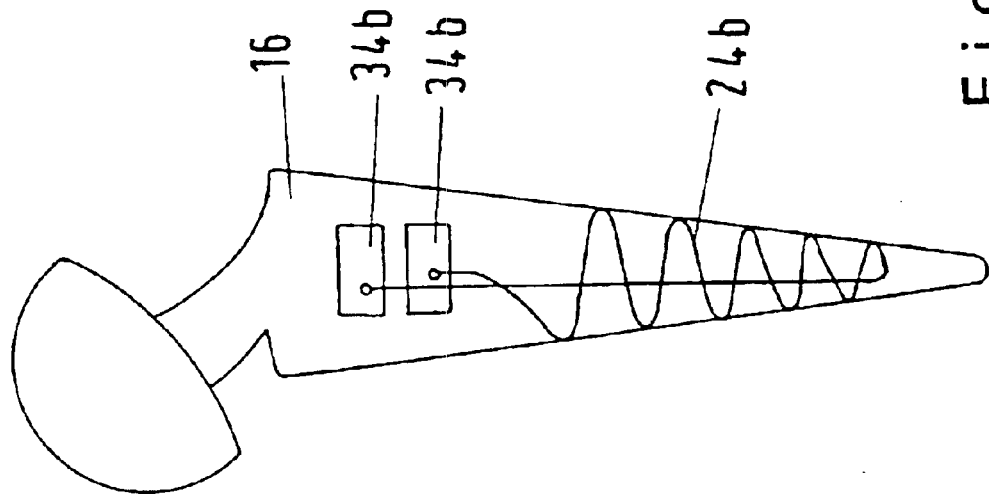
FIGS. 7a and 7b—two exemplary embodiments of a joint implant designed according to the invention.
Figure 7B:
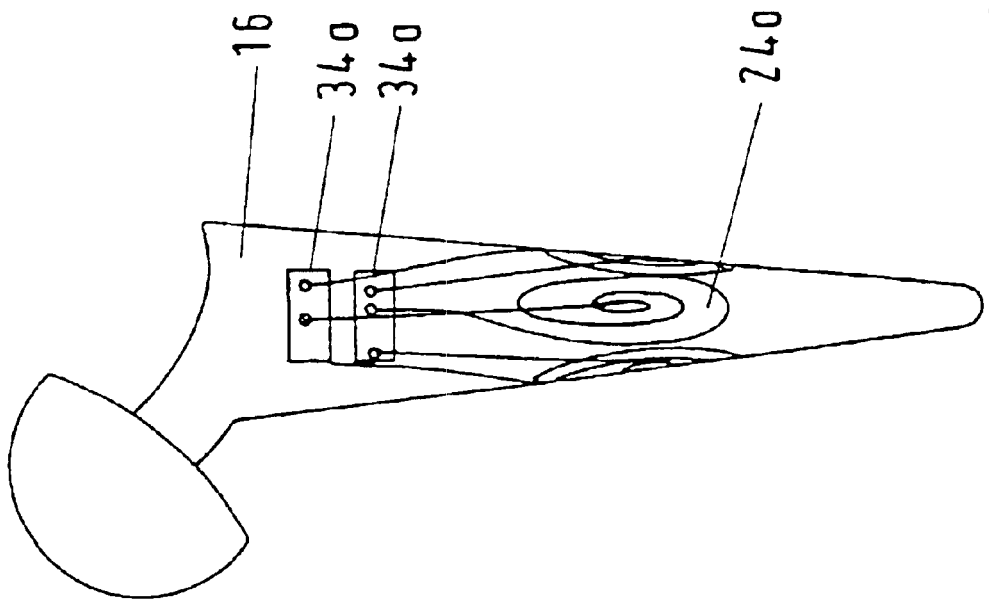

FIGS. 7a and 7b each depict a joint implant 16 with an integrated resonance circuit. The structure and arrangement of the inductors 24a, 24b and capacitors 34a, 34b correspond substantially to those of FIGS. 6a and 6b. The capacitor 34a, 34b is in each case designed in the form of two plates arranged one above the other (alternatively: next to each other).

Figure 8B:
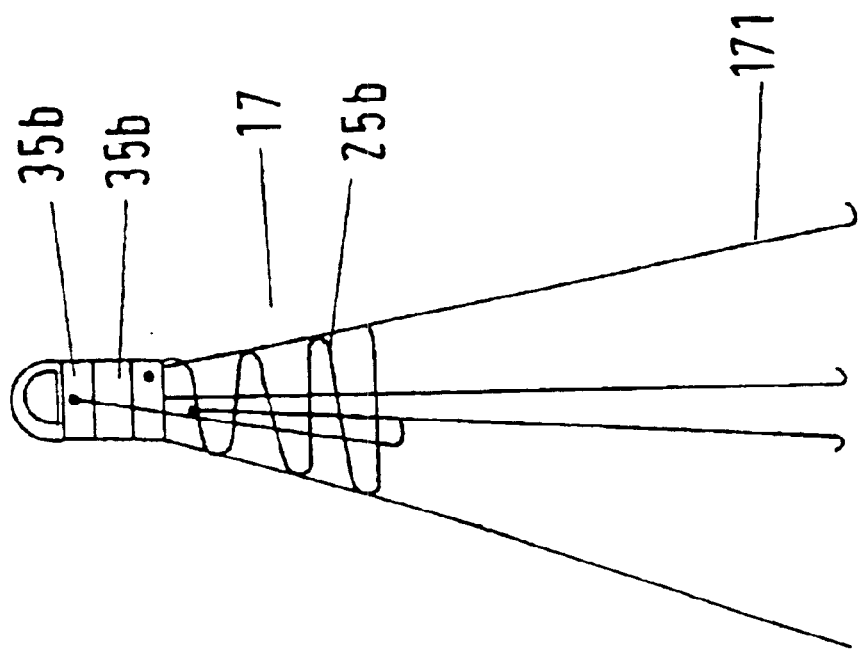
FIGS. 8a and 8b—two exemplary embodiments of a vena cava filter designed according to the invention.
Figure 8A:
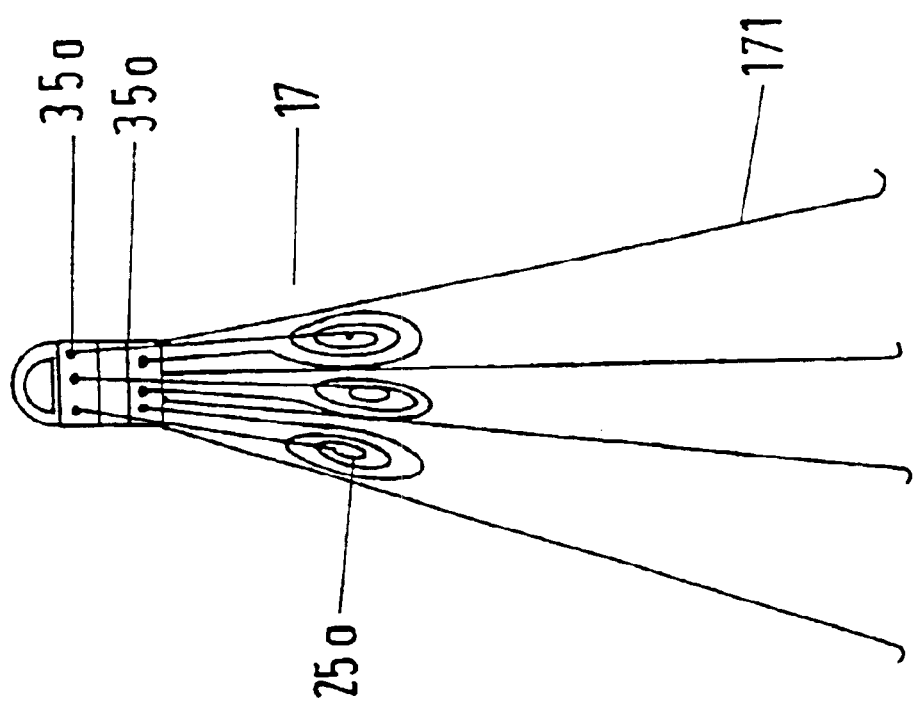

In FIGS. 8a and 8b, a resonance circuit is formed in each case on a vena cava filter 17. A vena cava filter is used in particular in a vein for protection against venous thrombosis as a type of funnel. The filter is attached to the vessel wall by means of toothed elements 171. The inductor 25a, 25b is again spiral-shaped (FIG. 8a) or helix-shaped (FIG. 8b). The capacitor 35a, 35b is, for example, again formed by parallel, annular capacitive elements.

The inductors 25a, 25b are preferably cut from metal sheet by laser. They are attached in a suitable manner to the toothed elements 171 and also provide stabilization.

It is likewise possible to form the inductors 25a, 25b and possibly also the capacitors 35a, 35b from the material of the vena cava filter 17. The filter and inductors/capacitors are, for instance, cut from a suitable conducting material by known laser or spark erosion or waterjet cutting techniques.

Figure 9B:
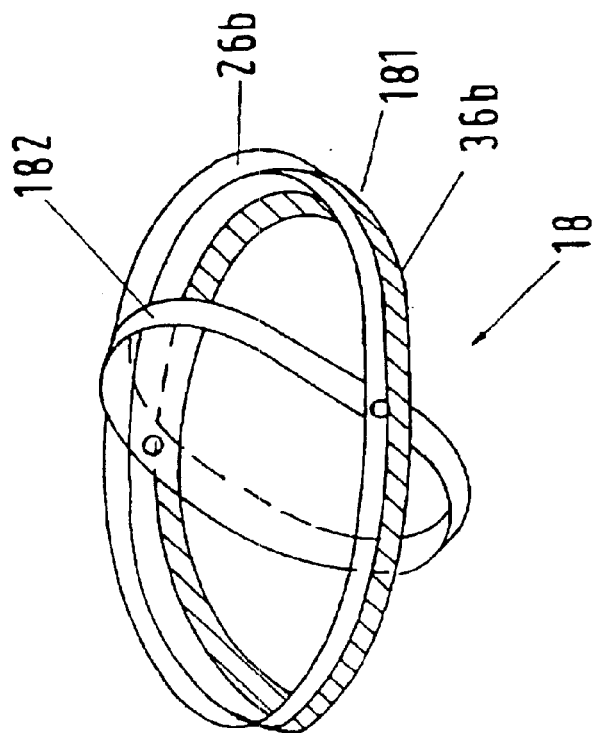
FIGS. 9a and 9b—two exemplary embodiments of a cardiac valve designed according to the invention.
Figure 9A:
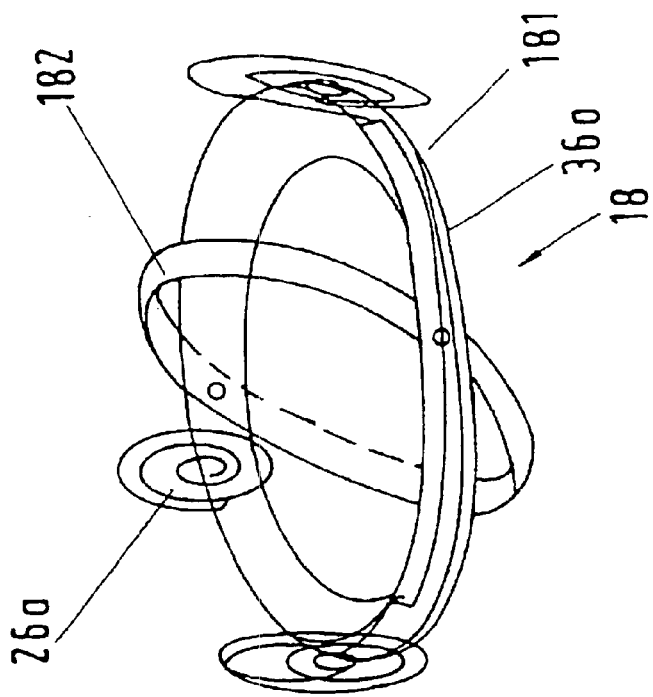

And finally, FIGS. 9a and 9b depict a cardiac valve 18 with a ring 181 which is sutured into the cardiac tissue and on which the actual cardiac valve 182 is arranged. To form a resonance circuit which effects an amplified excitation of the nuclear spin, a condenser 36a, 36b is integrated into the ring 181, for instance, in the shape of parallel annular conductors. In FIG. 9a, solenoid coils 26a, which unfold on the circumference of the ring, are provided as inductors. In FIG. 9b, a toroidal coil 26b is integrated into the ring 181 in addition to the condenser 36b as the inductor of the resonance circuit.

It is noted that with regard to the exemplary embodiments in FIG. 1a, 1b through 9a, 9b, a combination of the various coil arrangements may also be provided in each case.

In a variant of the device according to the invention (not depicted), the device is also used in flow measurements, if a fluid flows through or around it such as, for instance, the vena cava filter of FIG. 8. The device then preferably has two resonance circuits arranged following each other whereby the first resonance circuit has two crossed diodes in accordance with FIG. 2e such that the capacitance is short circuited during excitation, whereas the second resonance circuit is formed without diodes. This results in the fact that during application of high-frequency MR excitation impulses to a subsection of the device, which subsection is surrounded by the resonance circuit without diodes, amplified excitation takes place. However, in the other subsection that is surrounded by the resonance circuit with diodes, a changed signal response now exists compared to the surrounding tissue, as was disclosed with reference to FIG. 2e. With the application of suitable sequence techniques, such an arrangement is particularly effective for the determination of flow and thus for the functional control of the device.

In a further development of the invention (not depicted), provision is made that the inductor of the device itself is used as a receptor coil for the acquisition of MR response signals, whereby the inductor is connected via cable connection to extracorporeal function components. It thus becomes possible to use the inductor of the resonance circuit increasingly actively for the imaging. Due to the necessity of a cable connection to extracorporeal function components this will, however, in general only be possible during a surgical procedure.

The invention is not limited in its embodiment to the previously disclosed exemplary embodiments. Rather, a number of variants which make use of the invention even with fundamentally different types of embodiments, is conceivable.

What is claimed is:

1. An MR imaging method for imaging and determining the position of a medical device, the medical device having a passive resonance circuit with an inductor and a capacitor, the inductor being integrated into or formed by an unfolding portion of the medical device that at least in part is capable of being unfolded when inserted in an examination object, the method comprising:
    arranging the examination object in an external magnetic field,
    applying high-frequency radiation having a specific resonance frequency essentially equal to a resonance frequency of the passive resonance circuit so that transitions between spin energy levels of the atomic nuclei of the examination object are excited, and MR signals are produced,
    detecting the MR signals as signal responses, which are evaluated and imaged in spatial resolution,
    unfolding the unfolding portion of the device after insertion into the examination object such that the inductor formed by or integrated into the unfolding portion unfolds along with the unfolding portion,
    producing, by means of the device, a changed signal response of the examination object in a locally defined area, and
    detecting the changed signal response of the examination object to determine the position of the medical device.

2. The method according to claim 1 wherein the application of the high-frequency radiation excites the resonance circuit so that the excitation of the nuclear spins of the examination object is amplified in the locally defined area.

3. The method according to claim 2 wherein the locally defined area where the amplification of the excitation of the nuclear spins takes place is located in a compartment formed within the device and surrounded by the inductor.

4. The method according to claim 2 wherein the locally defined area where the amplification of the excitation of the nuclear spins takes place is outside the device and adjacent thereto, and wherein at least one resonance circuit is arranged on the surface of the device such that with the application of high-frequency radiation, the magnetic flow in the adjacent area is amplified.

5. The method according to claim 1 wherein when high-frequency radiation is applied to the resonance circuit, the circuit becomes detuned or the capacitor is short circuited to the extent that no amplified excitation of the nuclear spins takes place in the locally defined area, but wherein when the signal response of the locally defined area is measured, the detuning of the resonance circuit or the short circuiting of the capacitance is canceled and results in a change in the signal response.

6. The method according to claim 1, 2, 3, 4, or 5 wherein the resonance circuit is adjusted to the resonance frequency by unfolding the device after insertion of the device into the examination object.

7. The method according to claim 1 wherein at least one of the inductor and the capacitor are adjusted for the resonant tuning of the resonance circuit.

8. The method according to claim 1 wherein the device has at least two resonance circuits whose inductors have coils, and wherein the coils of the respective inductors are oriented differently from each other.

9. The method according to claim 8 wherein the inductors are aligned one of perpendicularly to each other and behind each other.

10. The method according to claim 1 wherein the medical device is selected from a vena cava filter or a balloon catheter.

11. A medical device that at least in part is capable of being unfolded comprising:
    at least one passive resonance circuit having an inductor and a capacitor, whose resonance frequency is essentially equal to a resonance frequency of an MR imaging system's applied high-frequency radiation, wherein the at least one passive resonant circuit shifts excitation of spin energy levels of atomic nuclei of an examination object to generate an enhanced MR signal in a locally defined area, and wherein a part of the device that is capable of being unfolded forms the inductor or the inductor is integrated into such a part, such that the inductor unfolds along with the device when the device is unfolded.

12. The device according to claim 11, wherein the inductor is formed or arranged on the surface of the device.

13. The device according to claim 11 or 12, wherein the inductor is formed by a conductor which runs on the surface of the device.

14. The device according to claim 13, wherein the inductor is formed on a foil which is adhered to the surface of the device.

15. The device according to claim 12, wherein the inductor is formed from the material of the device.

16. The device according to claim 11, wherein the device is elongated in shape and has a longitudinal axis, the inductor is formed as a coil having an axis, and the axis of the inductor runs substantially parallel to the longitudinal axis of the device.

17. The device according to claim 16, wherein the inductor is formed by a conductor arranged on the surface of the device in the shape of at least a single helix.

18. The device according to claim 17 wherein the helix is a double or multiple helix.

19. The device according to claim 11, wherein the device is elongated in shape and has a longitudinal axis, the inductor is formed as a coil having an axis, and the axis of the inductor runs substantially perpendicular to the longitudinal axis of the device.

20. The device according to claim 19, wherein the inductor is formed by a spiral-shaped conductor formed or arranged on the surface of the device.

21. The device according to claim 11, wherein the device has a plurality of resonance circuits with a plurality of inductors.

22. The device according to claim 21 wherein the plurality of inductances are arranged perpendicularly relative to each other or arranged behind each other.

23. The device according to claim 11, wherein the device has means for detuning at least one resonance circuit with the application of high-frequency radiation.

24. The device according to claim 23, wherein the detuning means are designed such that they switch a coil parallel to the inductor of the resonance circuit with the application of high-frequency radiation.

25. The device according to claim 23, wherein the detuning means are designed such that they switch a condenser parallel to the capacitor of the resonance circuit with the application of high-frequency radiation.

26. The device according to claim 11, wherein the device is provided with means to short circuit the capacitor when applying high-frequency radiation.

27. The device claim 26, wherein the means for short circuiting the capacitor comprises two diodes which are switched parallel to the capacitor.

28. The device according to claim 11, wherein a switch is provided by which the at least one resonance circuit can be activated or deactivated.

29. The device according to claim 11, wherein at least one of the inductor and capacitor of the resonance circuit are adjustable for tuning to the resonance frequency of the MR system.

30. The device according to claim 11, wherein the resonance circuit has a plurality of parallel or serially switched inductors and/or capacitors.

31. The device according to claim 11, wherein the device is a balloon catheter having an axis and an outer skin on which a spiral-shaped or helix-shaped inductor is formed.

32. The device according to claim 31, wherein the capacitor is in the form of parallel conductors which run along the axis of the balloon catheter.

33. The device according to claim 11, wherein the device is a vena cava filter having-elongated, movable toothed elements and the inductor is attached to the toothed elements.

34. The device according to claim 33, wherein at least one of the inductor and capacitor are made of the same material as the vena cava filter.

35. The medical device according to claim 11, selected from a vena cava filter or a balloon catheter.

36. An MR imaging system for imaging an examination object having a medical device inserted therein, the medical device having a passive resonance circuit with an inductor and a capacitor, the inductor being integrated into or formed by an unfolding portion of the medical device that at least in part is capable of being unfolded when inserted in the examination object, the imaging system comprising:

an imaging apparatus adapted to apply high-frequency radiation having a specific resonance frequency essentially equal to the resonance frequency of the passive circuit so that transitions between spin energy levels of the atomic nuclei of the examination object are excited, and MR signals are produced, the imaging apparatus being further adapted to detect the MR signals as signal responses, which are evaluated and imaged in spatial resolution, wherein the medical device modifies the transitions between spin energy levels of the atomic nuclei of the examination object to change the signal response of the examination object in a locally defined area and wherein the imaging apparatus is further adapted to detect the changed signal response of the examination object to determine the position of the medical device.

37. An MR imaging system comprising:

a medical device that at least in part is capable of being unfolded, the medical device comprising, at least one passive resonance circuit having an inductor and a capacitor, whose resonance frequency is essentially equal to a resonance frequency of an MR imaging system's applied high-frequency radiation, wherein the at least one passive resonant circuit shifts excitation of spin energy levels of atomic nuclei of an examination object to generate an enhanced MR signal in a locally defined area, and wherein a part of the device that is capable of being unfolded forms the inductor or the inductor is integrated into such a part, such that the inductor unfolds along with the device when the device is unfolded.

38. An MR imaging method for imaging and determining position of a medical device, the medical device having a passive resonance circuit with an inductor and a capacitor, the inductor being integrated into an unfolding portion of the medical device which is unfoldable in an examination object under examination, the method comprising:

applying high-frequency radiation to an examination object after the medical device is unfolded therein such that the inductor integrated into the unfolding portion unfolds along with the unfolding portion, the high frequency radiation having a specific resonance frequency approximately equal to a resonance frequency of the passive resonance circuit to excite transitions between spin energy levels of the atomic nuclei of the examination object, and produce MR signals, exciting the resonance circuit, wherein the excited resonance circuit amplifies the excitation of transitions between spin energy levels of the atomic nuclei of the examination object in a locally defined area to produce amplified MR signals; and detecting the amplified MR signals to determine the position of the medical device.

39. The method of claim 38 further comprising unfolding the unfolding portion of the device, after insertion into the examination object, along with the inductor.

40. The method of claim 38 further comprising adjusting the resonance frequency of the passive resonance circuit by unfolding the unfolding portion of the device, after insertion into the examination object, along with the inductor.

41. A medical device for use in an MR imaging system, the medical device comprising, a passive resonance circuit having an inductor and a capacitor, the inductor being integrated into an unfolding portion of the medical device, such that the inductor unfolds with the unfolding portion of the medical device after insertion in an examination object, wherein a resonance frequency of the passive resonance circuit us approximately equal to a resonance frequency of radiation applied by the MR imaging system.

42. The medical device of claim 41 wherein the passive resonant circuit shifts excitation of spin energy levels of atomic nuclei of an examination object to generate an enhanced MR signal in a locally defined area.

* * * * *